United States Patent [19]

Hilti et al.

[11] Patent Number: 5,387,627
[45] Date of Patent: Feb. 7, 1995

[54] RADICAL CATION SLATS OF TETRATHIOTETRACENE AND COPPER CHLORIDE, THEIR PREPARATION AND THE USE THEREOF

[75] Inventors: Bruno Hilti, Basel; Ernst Minder, Sissach; Carl W. Mayer, Riehen, all of Switzerland; Bernd Klingert, Inzlingen, Germany

[73] Assignee: Ciba-Geigy Corporation, Ardsley, N.Y.

[21] Appl. No.: 153,247

[22] Filed: Nov. 16, 1993

Related U.S. Application Data

[62] Division of Ser. No. 906,074, Jun. 29, 1992, Pat. No. 5,284,600.

[30] Foreign Application Priority Data

Jul. 2, 1991 [CH] Switzerland ............... 1952/91-8

[51] Int. Cl.⁶ .................................................. C08K 5/45
[52] U.S. Cl. .................................. 524/84; 428/704
[58] Field of Search ............................. 524/84; 428/704

[56] References Cited

U.S. PATENT DOCUMENTS

| | | | |
|---|---|---|---|
| 4,384,025 | 5/1983 | Hilti et al. | 428/411 |
| 4,617,151 | 10/1986 | Mayer et al. | 540/1 |
| 5,009,812 | 4/1991 | Finter et al. | 252/500 |
| 5,108,841 | 4/1992 | Wegmann et al. | 252/518 |
| 5,158,829 | 10/1992 | Wegmann et al. | 428/411.1 |

FOREIGN PATENT DOCUMENTS

| | | |
|---|---|---|
| 285564 | 10/1988 | European Pat. Off. |
| 2641742 | 3/1977 | Germany |
| 3510092 | 9/1985 | Germany |

OTHER PUBLICATIONS

I. F. Shchegdeu et al. Extended Linear Chain Compounds vol. 2, pp. 393-394 (1982).

Chem. Abst. vol. 94, No. 4, 22829v (1982), M. Masseen et al.

L. C. Issett, et al. "Ion-Radical Salts of Tetrathiotetracene", Annals New York Academy of Sciences, vol. 313, p. 395 (1978).

*Primary Examiner*—Kriellion S. Morgan
*Attorney, Agent, or Firm*—George R. Dohmann

[57] ABSTRACT

Radical cation salts having the composition of formula I

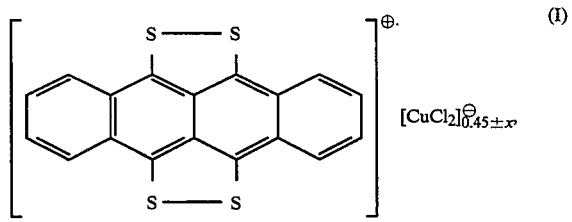

wherein x has a value from −0.1 to +0.2.

These radical cation salts crystallize in needle form and are electric conductors. They can be incorporated in polymers to form conductive networks of crystal needles in a polymer matrix. The polymers can be used for making antistatically treated mouldings or electrodes.

11 Claims, No Drawings

RADICAL CATION SLATS OF TETRATHIOTETRACENE AND COPPER CHLORIDE, THEIR PREPARATION AND THE USE THEREOF

This is a divisional of Ser. No. 07/906,074, filed Jun. 29, 1992 now U.S. Pat. No. 5,284,600.

The present invention relates to radical cation salts of tetrathiotetracene (hereinafter abbreviated to TTT) and $CuCl_2$, to a process for their preparation by oxidation of TTT in organic solvents with anhydrous $CuCl_2$, to $CuCl_2$ aquo complexes or $CuCl_2$ solvent complexes, and to the use thereof as electric conductors, typically for providing polymers with an antistatic finish or for making conductive films, sheets, coatings or mouldings.

In a general article in Extended Linear Chain Compounds, Vol. 2, Editor J. S. Miller. Plenum Press New York, pages 393 and 394 (1982), I. F. Shchegdev et al. describe radical cation complexes of TTT and $CuBr_2$ as well as of tetraselenotetracene and $CuCl_2$. The conductivity of these complexes is quite low, even in the case of monocrystals. The specific conductivity $\sigma$ at 300 K is given as $10^{-2}$ to $10^{-3}$ $\Omega^{-1}$. High conductivities in radical cation complexes of this kind are usually observed if the anion contains bromine or iodine. The thermal resistance of such complexes, however, is low.

Surprisingly, it has now been found that the conductivity of radical cation salts of TTT and $CuCl_2$ is up to two orders of magnitude higher, and that these salts have in addition substantially greater thermal stability and thus can be processed even at higher temperatures. These salts crystallise in needle form and can be used for constructing networks of crystal needles in a polymer matrix. These salts also differ in their composition surprisingly and markedly from the known complexes referred to above.

In one of its aspects the invention relates to radical cation salts having the composition of formula I

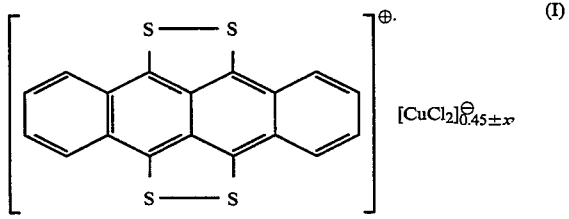

wherein x has a value from $-0.1$ to $+0.2$.

The value of x depends essentially on the synthesis conditions, mainly on the solvent employed, the kind of starting materials and their ratios. Preferably the value of x is $-0.05$ to $+0.15$, more particularly 0.05 to $+0.1$ and, most preferably, $-0.05$ to $+0.05$. Especially preferred are radical cation salts of formula I, wherein the value of x is $-0.02$.

In another of its aspects, the invention relates to a process for the preparation of radical cation salts of formula I, which comprises reacting anhydrous $CuCl_2$, a $CuCl_2$ aquo complex or a $CuCl_2$ solvent complex, in an organic solvent, with tetrathiotetracene.

The copper dichloride, copper dichloride hydrates or copper dichloride solvent complexes are preferably used in an amount of 0.3 to 0.8 mol, most preferably 0.35 to 0.6 tool, per mol of tetrathiotetracene.

When using anhydrous copper dichloride, water may be added to the reaction mixture, conveniently in the form of an aqueous solvent.

Very numerous solvent complexes of copper dichloride and polar aprotic or polar protic solvents are known. It is possible to use monomeric, dimeric and polymeric complexes. Suitable solvents are mainly those containing hetero atoms, typically oxygen, sulfur, phosphorus and nitrogen. Representative examples are ethers (diethyl ether, dibutyl ether, ethylene glycol dimethyl or diethyl ether), esters and lactones (ethyl acetate, γ-butyrol-actone), sulfones (dimethyl sulfone, tetramethylene sulfone) and amines (pyridine, α-pyridone, α-methyl pyridine, ethylenediamine, N,N-dimethylethylenediamine, 1-(β-aminoethyl)pyridine, 1-(β-methylaminoethyl)pyridine.

The reaction is carried out in the presence of an inert solvent. Exemplary of suitable solvents, which can be used singly or as a mixture of solvents, are aliphatic and aromatic hydrocarbons, typically hexane, cyclohexane, methyl cyclohexane, benzene, nitrobenzene, toluene, xylene and biphenyl; alcohols such as methanol, ethanol, propanol and butanol; ethers such as diethyl ether, diethylene glycol dimethyl ether, ethylene glycol dimethyl ether, diphenyl ether, tetrahydrofuran and dioxane; halogenated hydrocarbons such as methylene chloride, chloroform, 1,1,2,2-tetrachloroethane and chlorobenzene; esters and lactones such as ethyl acetate, butyrolactone, valerolactone; carboxamides and lactams such as dimethyl formamide, dimethyl acetamide and N-methylpyrrolidone. If the reactants are sparingly soluble, they can be used in the form of suspensions in a solvent.

The inventive process is conveniently carried out at elevated temperature, typically in the range from 30° to 300° C., preferably 50° to 250° C. The procedure may conveniently comprise adding a solution of the copper compound to a hot solution of tetrathiotetracene and then allowing the reaction mixture to cool. The crystalline precipitate is then isolated by filtration and, if desired, purified by washing and dried. If larger crystals are desired, a diffusion-controlled reaction is carried out by separating the solid reactants separately in the storage vessels of a reactor and then covering them with a solvent. The radical cation salts are obtained in high purity.

The novel radical cation salts are thermally very stable and can also be incorporated in plastics materials at elevated temperature. A good antistatic finish is obtained on account of the high conductivity in moulded articles ($\sigma$ of the compressed powder $=0.4$ to 2,0 $\Omega^{-1}\cdot cm^{-1}$). The ability of these radical cation salts to form needle-shaped crystals makes it possible to obtain moulded parts such as coatings or self-supporting films of high conductivity which may be up to 40 % of the conductivity of the novel crystalline radical cation salts. The preparation can be effected in simple manner by adding the tetrathiotetracene and the copper compound to a molten polymer which is cooled after shaping, or by addition to a solution of the polymer and removing the solvent by evaporation after processing. The dense, fine-meshed networks of crystal needles obtained in a polymer matrix result in a high conductivity.

In yet another of its aspects, the invention relates to a composition comprising a) a thermosetting, thermoplastic or structurally crosslinked polymer, and b) a radical cation salt of formula I in the form of a network of crystal needles in the polymer matrix.

The composition may contain the radical cation salt in an amount of 0.01 to 30% by weight, preferably 0.01 to 20%, more particularly 0.01 to 10% by weight and, most preferably, 0.1 to 5% by weight.

The thermoplastic polymers may be selected from the following polymers, copolymers or mixtures thereof:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1) above, for example polypropylene/ethylene propylene copolymers, LDPE/EVA, LDPE/EAA. LLDPE/EVA and LLDPE/EAA.

3a. Hydrocarbon resins (for example $C_5$–$C_9$), including hydrogenated modifications thereof (for example tackifiers).

4. Polystyrene, poly-(p-methylstyrene), poly-($\alpha$-methylstyrene).

5. Copolymers of styrene or $\alpha$-methylstyrene with dienes or acrylic derivatives, for example styrene/butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or $\alpha$-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example poly- vinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from $\alpha\beta$-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer, polyacetals modified with thermoplastic polyurethanes, acrylates or MBS.

13. Polyphenylene oxides and sulfides and mixtures thereof with polystyrene or polyamides.

14. Polyurethanes which are derived from polyethers, polyesters or polybutadienes carrying terminal hydroxyl groups on the one hand and aliphatic or aromatic polyisocyanates on the other,-as well as precursors thereof.

15. Polyamides and copolyamides which are derived from diamines and dicarboxylic acids and[ch] or from aminocarboxylic acids or the corre-sponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer as modifier, for example poly-2,4,4,-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylolcyclohexane terephthalate, polyhydroxybenzoates as well as block-copolyether esters derived from hydroxyl-terminated polyethers; and also polyesters modified with polycarbonates or MBS.

18. Polycarbonates and polyester carbonates.

19. Polysulfones, polyether sulfones and polyether ketones.

20. Polyethers of diglycidyl compounds, including diglycidyl ethers and diols, for example of bisphenol A diglycidyl ether and bisphenol A.

21. Natural polymers such as cellulose, rubber, gelatine and chemically modified homologous derivatives thereof such as cellulose acetates, cellulose propionates and cellulose butyrates, or the cellulose ethers, such as methylcellulose; as well as rosins and their derivatives.

22. Mixtures (polyblends) of the aforementioned polymers, for example PP/EPDM, Polyamide 6/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPO.

Preferred thermoplastic polymers are polyolefins, polystyrene, polyvinyl chloride, polyvinylidene chloride, polyvinylidene fluoride, polyacrylates, polymethacrylates, polyamides, polyesters, polycarbonates, aromatic polysulfones, aromatic polyethers, aromatic polyether sulfones, polyimides and polyvinyl carbazole.

The thermosetting and structurally crosslinked polymers may be typically the following polymers:

1. Crosslinked polymers which are derived from aldehydes on the one hand and phenols, ureas and melamines on the other hand, such as phenol/formaldehyde resins, urea/formaldehyde resins and melamine/formaldehyde resins.

2. Drying and non-drying alkyd resins.

3. Unsaturated polyester resins which are derived from copolyesters of saturated and unsaturated dicarboxylic acids with polyhydric alcohols and vinyl compounds as crosslinking agents, and also halogen-containing modifications thereof of low flammability.

4. Crosslinkable acrylic resins derived from substituted acrylic esters such as epoxy acrylates, urethane acrylates or polyester acrylates.

5. Alkyd resins, polyester resins or acrylate resins which are cross-linked with melamine resins, urea resins, polyisocyanates or epoxy resins.

6. Rubber derived from crosslinked polydienes, for example butadiene or isoprene; silicon rubber.

7. Crosslinked epoxy resins which are derived from polyepoxides, for example from bisglycidyl ethers or from cycloaliphatic diepoxides, and which may contain a hardener as crosslinking agent or which are crosslinked thermally using curing accelerators or by irradiation.

Among the crosslinked polymers, crosslinked epoxy resins are preferred which, as polyepoxides, are derived preferably from glycidyl compounds which contain on average two epoxy groups in the molecule. Particularly suitable glycidyl compounds are those which contain two glycidyl groups, β-methylglycidyl groups or 2,3-epoxycyclopentyl groups attached to a hetero atom (e.g. sulfur, preferably oxygen or nitrogen), in particular bis(2,3-epoxycyclopentyl) ether; diglycidyl ethers of polyhydric aliphatic alcohols, such as 1,4-butanediol, or polyalkylene glycols, such as polypropylene glycols; diglycidyl ethers of cycloaliphatic polyols, such as 2,2-bis(4-hydroxycyclohexyl)propane; diglycidyl ethers of polyhydric phenols, such as resorcinol, bis(p-hydroxyphenyl)methane, 2,2-bis(p-hydroxyphenyl)propane (=diomethane), 2,2-bis(4'-hydroxy-3', 5'-dibromophenyl)propane, 1,3-bis(p-hydroxyphenyl)ethane; bis(β-methylglycidyl) ethers of the above dihydric alcohols or dihydric phenols; diglycidyl esters of dicarboxylic acids, such as phthalic acid, terephthalic acid, Δ4-tetrahydrophthalic acid and hexahydrophthalic acid; N,N-diglycidyl derivatives of primary amines and amides and heterocyclic nitrogen bases which contain two N-atoms, and N,N'-diglycidyl derivatives of disecundary diamides and diamines, such as N,N-diglycidylaniline, N,N-diglycidyltoluidine, N,N-diglycidyl-p-aminophenyl methyl ether, N,N'-dimethyl-N,N'-diglycidylbis(p-aminophenyl)methane; N',N''-diglycidyl-N-phenyl-isocyanurate; N,N'-diglycidyl ethyleneurea; N,N'-diglycidyl-5,5-dimethylhydantoin, N,N'-diglycidyl-5-isopropyl-hydantoin, N,N-methylenebis(N', N'-diglycidyl-5,5-dimethylhydantoin), 1,3-bis(N-glycidyl-5,5-dimethylhydantoin)-2-hydroxypropane; N,N'-diglycidyl-5,5-dimethyl-6-isopropyl-5,6-dihydrouracil, triglycidyl isocyanurate.

A preferred group of epoxy resins comprises glycidylated novolaks, hydantoins, aminophenols, bisphenols and aromatic diamines or cycloaliphatic epoxy compounds. Particularly preferred epoxy resins are glycidylated cresol novolaks, bisphenol A and bisphenol F diglycidyl ether, hydantoin-N,N'-bisglycide, p-aminophenol triglycide, diaminodiphenylmethane tetraglycide, vinylcyclohexene dioxide, 3,4-epoxycyclohexylmethyl-3,4-epoxycyclohexanecarboxylate or mixtures thereof.

Further suitable epoxy resins are prereacted adducts of such epoxy compounds with epoxy hardeners, for example an adduct of bisphenol A diglycidyl ether and bisphenol A, or adducts which have been prereacted with oligoesters which carry two terminal carboxyl groups and epoxides.

Suitable hardeners for epoxy resins are acid or basic compounds. Illustrative examples of suitable hardeners are: polyhydric phenols (resorcinol, 2,2-bis(4-hydroxyphenyl)propane) or phenol-formaldehyde resins; polybasic carboxylic acids and the anhydrides thereof, such as phthalic anhydride, tetrahydrophthalic anhydride, hexahydrophthalic anhydride, 4-methylhexahydrophthalic anhydride, 3,6-endomethylene-tetrahydrophthalic anhydride, 4-methyl-3,6-endomethylen-tetrahydrophthalic anhydride (methylnadic anhydride), 3,4,5,6,7,7-hexachloroendomethylene-tetrahydrophthalic anhydride, succinic anhydride, adipic anhydride, trimethyladipic anhydride, sebacic anhydride, maleic anhydride, dodecylsuccinic anhydride, pyromellitic dianhydride, trimellitic anhydride, benzophenonetetracarboxylic dianhydride, or mixtures of such anhydrides.

A preferred group of hardeners comprises novolaks and polycarboxylic anhydrides.

The epoxy resins can also be additionally cured with curing accelerators or only with thermal curing catalysts. Exemplary of curing accelerators and catalysts are 3-ethyl-4-methylimidazole, triamylammonium phenolate; mono- or polyphenols (phenol, diomethane, salicylic acid); boron trifluoride and the complexes thereof with organic compounds, such as boron trifluoride ether complexes and boron trifluoride amine complexes (BF$_3$/monoethylamine complex); phosphoric acid and triphenylphosphite.

Curing accelerators and catalysts are normally added in an amount of 0.1 to 10% by weight, based on the epoxy resin. Hardeners for epoxy resins are normally used in equimolar amounts, based on the epoxy groups and functional groups of a hardener.

Further additives for enhancing processing properties, the mechanical, electrical and thermal properties, surface properties and light stability can be blended into the novel formulation. Exemplary of such additives are finely particulate fillers, reinforcing fillers, plasticisers, lubricants and mould release agents, adhesion promoters, antistatic agents, antioxidants, heat and light stabilisers, pigments and dyes.

In a preferred embodiment, the novel compositions are shaped to mouldings, films, sheets, fibres, or to coatings on at least one surface of a substrate.

The novel compositions can be prepared by methods known in plastics technology. In shaping techniques for polymers, such as casting, compression moulding, injection moulding and extrusion, it is possible to add the radical cation salt itself to form suspensions, or to add TTT and the copper compound jointly to the polymer melt, to at least one starting material for thermosetting plastics, or separately to each starting material (for example to the epoxy resin and the hardener) to form solutions or suspensions, such that, after shaping, the radical cation salt crystallises or precipitates during cooling in the form of needles which form a network in a polymer matrix.

In a particularly preferred embodiment, the novel composition is in the form of a film or sheet or a coating on at least one surface of a substrate. Such embodiments are conveniently prepared by dissolving or suspending a thermoplastic polymer or at least one starring material for a thermosetting polymer or a structurally crosslinked polymer in a solvent or inert solvent, then applying the solution or suspension by known coating techniques to a substrate which may be preheated, and thereafter removing the solvent by heating, while crosslinkable mixtures can then be cured. Self-supporting films and sheets are obtained by peeling the coating from the substrate or by extrusion.

Examples of suitable substrates are glass, metals, plastics, mineral and ceramic materials, wood and paper. The substrates may be of any external shape and are typically mouldings, filaments, fibres, fabrics, bars, pipes, ribbons, sheets, boards, rolls or casings.

Suitable coating techniques are typically brushing, rolling, doctor coating, casting, spin coating, curtain coating and spraying. Spraying methods are especially preferred, as on the one hand very thin and uniform layers with substantially isotropic, very fine-mesh and homogeneous networks are obtainable from crystal needles of the radical cation salts and, on the other, the size of the crystal needles and the mesh width of the networks can be controlled by the droplet size, even when suspensions are sprayed.

Suitable inert solvents for polymers and starting materials for polymers are typically polar and, preferably, aprotic solvents, which may be used singly or in mixtures of at least two solvents. Representative examples of such solvents are: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyethyl acetate, $\gamma$-butyrolactone, $\delta$5-valerolactone, pivalolactone), carboxamides and lactams (N,N-dimethylformamide, N,N-diethylformamide, N,N-dimethylacetamide, tetramethylurea, hexamethylphosphoric triamide, $\gamma$-butyrolactam, $\epsilon$-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (N-methylpiperidine, N-methylmorpholine) substituted benzenes (benzonitrile, chlorobenzene, o-dichlorobenzene, 1,2,4-trichlorobenzene, nitrobenzene, toluene, xylene) and nitriles (acetonitrile, propionitrile).

The coating techniques can be conveniently carried out by dissolving the individual components separately and combining them just before application of the chosen technique. However, it is also possible to prepare two solutions of the components, for example polymer and TTT or copper compound, as well as copper compound or TTT, or to combine all the components in one solution. In this last mentioned case, the radical cation salts can crystallise out already prior to coating; but this has virtually no effect on the desired quality of the coating.

The solutions are preferably heated, conveniently to 50°–250° C. It is useful to heat the substrate as well to accelerate the removal of the solvent, which is normally effected in the temperature range from 50° to 200° C., until the coating is dry. If it is desired to detach the coatings to give self-supporting films or sheets, the substrate can be treated with antiblocking agents prior to coating.

An alternative coating method comprises suspending the novel radical cation salts, which are obtained as needle-shaped crystals, in a solution of a polymer or of starting materials for thermosetting polymers, then coating a substrate and afterwards removing the solvent, and, if appropriate, thereafter effecting a cure to form the thermosetting polymers. It is also possible to prepare dry powder mixtures from polymer powders or solid starting materials for thermosetting polymers and the radical cation salts, and to process these mixtures in coating or electrostatic coating methods to layers on substrates. Networks of crystal needles in a polymer matrix are also obtained in these alternative methods.

It is also possible to produce pure layers of networks of crystal needles of the CT complexes on a substrate by applying to a substrate solutions or suspensions of the CT complexes in a solvent and afterwards evaporating the solvent. Such layers can be electrochemically metallised to enhance the conductivity, conveniently with Cu, Pt or Pd. It can be useful to provide such pure layers with a protective coating of a polymer.

The layer thicknesses can vary over a wide range, depending on the choice of coating method. Spray methods give very thin layers, whereas thicker layers can also be obtained with brushing and casting methods. The layer thicknesses can be typically from 0.01 to 5000 $\mu$m, preferably from 0.1 to 1000 $\mu$m and, most preferably, from 0.1 to 500 $\mu$m.

Depending on the choice of polymer, the novel compositions are opaque or transparent and have outstanding properties. Thus, surprisingly, the coatings and mouldings have an excellent discharge capacity which, for heterogeneous materials, is otherwise difficult to achieve or cannot be achieved at all. The compositions are therefore especially suitable for use for making antistatically treated moulded parts for the electrostatic screening of components or for making antistatically treated mouldings. The high conductivities also permit the use of the novel compositions as electric conductors, for example as electrodes for display elements or electronic components. The compositions also have excellent mechanical strength and performance properties.

The following Examples illustrate the invention in more detail.

A) Preparation of the radical cation salts

Example A1: With stirring, 60 mg of (TTT) are dissolved in 33 g of γ-butyrolactone under argon at a bath temperature of 180° C. (green solution). Then a yellow solution of 15.3 mg of $CuCl_2.2H_2O$ in 5 g of γ-butyrolactone is added. The stirrer and the oil bath heating are switched off and the reaction solution is then cooled in the oil bath, whereupon needles crystallise (yield: 57 mg). The specific resistance of the crystals is 0.5 to 1 Ω·cm. The X-ray structural analysis shows that the product is the radical cation salt of the composition $TTT(CuCl_2)_{0.45}$.

Examples A2 to A8: The procedure of Example A1 is repeated, but without inert gas and replacing $CuCl_2.2H_2O$ by anhydrous $CuCl_2$ or solvent complexes.

Example A2: Solvent complex: $CuCl_2(dimethyl\ sulfoxide)_2$, composition $TTT(CuCl_2)_{0.44}$, $\sigma = 0.7273\ \Omega^{-1}\cdot cm^{-1}$.

Example A3: Solvent complex: $[CuCl_2(\alpha\text{-pyrrolidone})]_2$, composition $TTT(CuCl_2)_{0.43}$, $\sigma = 1.629\ \Omega^{-1}\cdot cm^{-1}$.

Example A4: Solvent complex: $[CuCl_2(\text{tetramethylene sulfone})]$ (polymer), composition $TTT(CuCl_2)_{0.44}$, $\sigma = 1.238\ \Omega^{-1}\cdot cm^{-1}$.

Example A5: Solvent complex: $CuCl_2(\alpha\text{-picoline})_2$, composition $TTT(CuCl_2)_{0.42}$, $\sigma = 1.02\ \Omega^{-1}\cdot cm^{-1}$.

Example A6: Solvent complex: $[CuCl_2(\text{butyrolactone})]$, (polymer) composition $TTT(CuCl_2)_{0.59}$, $\sigma = 1.597\ \Omega^{-1}\cdot cm^{-1}$.

Example A7: Solvent complex: $[CuCl_2(\text{butyrolactone})]$ (polymer), the solution contains 0.5% of water, composition $TTT(CuCl_2)_{0.51}$, $\sigma = 0.6954\ \Omega^{-1}\cdot cm^{-1}$.
Example A8: use of anhydrous $CuCl_2$ instead of solvent complex; composition $TTT(CuCl_2)_{0.44}$, $\sigma = 1.1\ \Omega^{-1}\cdot cm^{-1}$.

B) Use Examples

Example B1: 9.0 mg of TTT and 0.6 g of polycarbonate are dissolved at 160° C. in 18 g of γ-butyrolactone and the solution is mixed with a solution of 2.1 mg of $CuCl_2 2H_2O$ in 2 g of γ-butyrolactone. The reaction mixture is sprayed on to a preheated glass plate (spray conditions: glass nozzle with a diameter of 1 mm, propellant gas argon, distance of spray nozzle from glass plate c. 15 cm). The solvent is evaporated at 130° C. to leave a 8 μm layer with a fine needle network of conductive crystal needles of $TTT(CuCl_2)_{0.48}$ in a polycarbonate matrix. The specific resistance is $2.4 \cdot 10^3$ Ω·cm.

Example B2: 9.0 mg of tetrathiotetracene and 0.6 g of polycarbonate are dissolved at 150° C. in 16 g of anisole. To this solution is added a solution of 2.0 mg of $CuCl_2.2H_2O$ in 2 g of γ-butyrolactone. Small needles of the radical cation salt crystallise at once. The reaction mixture is sprayed onto a preheated glass plate (spray conditions as in Example B 1) and the solvent is evaporated at 100° C. The polycarbonate film is transparent and contains a fine, dense, conductive needle network. The specific resistance is $6 \cdot 10^3$ Ω·cm.

Measurement of the surface discharge:

The surface tension of c. 200 V is formed with the aid of a gold-plated tungsten wire of 50 micrometer diameter which is charged with a voltage of c. 3.4 kV. This voltage is so controlled that the current is kept at a constant 20 nA per cm wire length. The specimen is bonded with silver paste to a glass support and connected to a contact point at the edge of the support. In the course of an assay, the support shifts 8 mm under the corona wire at a speed of c. 50 cm/s and stops at the point where the contact point dips into an earthed conductive foam. The specimen then lies under a field strength meter (Isoprobe Electrostatic Voltmeter 244, Monroe Electronics Inc.). The decrease in the measured surface tension is stored with a digital oscilloscope. The sheets of Examples B1 and B2 are tested in this test. The surface tension is measured 0.5 second after the corona charge.

Result:

Example B 1: 2±1 volt; Example B2: 2±1 volt.

Example B3: 20.1 mg TTT and 2.5 g of polycarbonate are dissolved at 180° C. in 14.5 g of γ-butyrolactone. To this solution is added a solution of 5.5 mg of $CuCl_2.2H_2O$ in 1.5 g of γ-butyrolactone which contains 0.5% of water. After 30 seconds a film with a wet film thickness of 270 μm is drawn from this formulation with a coating knife on a glass plate. The solvent is then evaporated at 100° C. and the film is subsequently dried at 150° C. The specific resistance of the film is 500 to 800 Ω·cm and the film thickness is 23 μm.

Example B4: 15.27 mg of tetrathiotetracene and 3.75 g of a polyether of a diglycidyl ether of bisphenol A and bisphenol A are dissolved at 150° C. in 60 g of anisole. After about 30 minutes, 2.5 g of a solution of 3.75 mg of $CuCl_2.2H_2O$ and 2% of water in 2.5 g of γ-butyrolactone and 750 μl of an anisole solution containing 10% of a polyurethane oligomer (wetting agent) in xylene are added and mixed. The reaction mixture is sprayed on to a glass plate (spray conditions: bifluid nozzle of steel, propellant gas argon, distance of spray nozzle from glass plate c. 20 cm, spray rate 4 cm/s). The solvent is evaporated at 50° C. to leave a 5 μm layer with a dense network of conductive crystal needles of $TTT(CuCl_2)_{0.43}$ in a polyether matrix. The specific resistance is $2 \cdot 10^3$ Ω·cm.

Example B5: The coatings of Examples B1 and B3 are kept for 600 h at 85% relative humidity and at 85° C., and the resistance is measured by the four point method. The resistance remains virtually unchanged.

What is claimed is:

1. A composition comprising (a) a thermosetting, thermoplastic or structurally crosslinked polymer, and (b) a radical cation salt of formula I

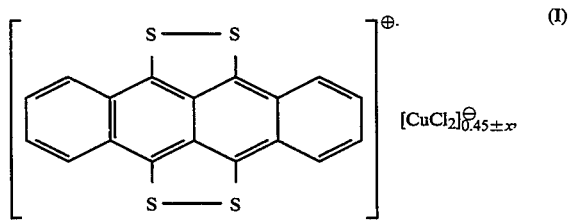

wherein x has a value of from −0.1 to +0.2; and wherein the radical cation salt is in the form of a network of needle crystals in the polymer.

2. A composition according to claim 1, which contains the radical cation salt in an amount of 0.01 to 30% by weight, based on said composition.

3. A composition according to claim 1, wherein the thermoplastic polymer is selected from the group consisting of polyolefins, polystyrene, polyvinyl chloride, polyvinylidene chloride, polyvinylidene fluoride, polyacrylates, polymethacrylates, polyamides, polyesters, polycarbonates, aromatic polysulfones, aromatic polyethers, aromatic polyether sulfones, polyimides and polyvinyl carbazole.

4. A composition according to claim 1, wherein the thermosetting polymer is an epoxy resin.

5. A composition according to claim 1 which is shaped into mouldings, films, sheets, fibres or a coating on at least one surface of a substrate.

6. A composition according to claim 5, wherein the layer thickness of the coating is 0.01 to 5000 μm.

7. A composition according to claim 5, wherein the layer thickness of the coating is 0.1 to 1000 μm.

8. A composition according to claim 1, wherein the value of x in formula I is −0.05 to +0.15.

9. A composition according to claim 1, wherein the value of x in formula I is 0.05 to +0.1.

10. A composition according to claim 1, wherein the value of x in formula I is −0.05 to +0.05.

11. A composition according to claim 1, wherein the value of x in formula I is −0.02.

* * * * *